United States Patent [19]

Shibahara et al.

[11] Patent Number: 5,206,384
[45] Date of Patent: Apr. 27, 1993

[54] ACTINONIN DERIVATIVES AND PHARMACEUTICALLY ACCEPTABLE SALTS THEREOF

[75] Inventors: Seiji Shibahara; Yoshiyuki Koyama; Shigeharu Inoue; Mitsugu Hachisu; Shinichi Kondo, all of Yokohama; Takaaki Aoyagi, Fujisawa; Tomio Takeuchi, Tokyo, all of Japan

[73] Assignees: Zaidan Hojin Biseibutsu Kagaku Kai; Meiji Seika Kaisha Ltd., both of Japan

[21] Appl. No.: 754,543

[22] Filed: Sep. 4, 1991

[30] Foreign Application Priority Data

Sep. 4, 1990 [JP] Japan .................... 2-232469

[51] Int. Cl.$^5$ ............................ C07D 207/08
[52] U.S. Cl. ........................ 548/537; 548/533; 548/540
[58] Field of Search ............ 548/533, 537, 540

[56] References Cited

U.S. PATENT DOCUMENTS

| | | | |
|---|---|---|---|
| 3,240,787 | 3/1966 | Singh et al. | 548/540 X |
| 4,663,342 | 5/1987 | Umezawa et al. | 514/423 |
| 4,929,633 | 5/1990 | Shibahara et al. | 548/540 X |

OTHER PUBLICATIONS

C.A. 108(19):167973e3, Hoffmann–Laroche (1987).

*Primary Examiner*—Joseph Paul Brust
*Attorney, Agent, or Firm*—Larson and Taylor

[57] ABSTRACT

A novel actinonin derivative and a salt thereof are provided, which are useful as enzyme inhibitors and particularly have strong inhibitory activities against enkephalinase and angiotensin-converting enzymes. This actinonin derivative is represented by general formula (I):

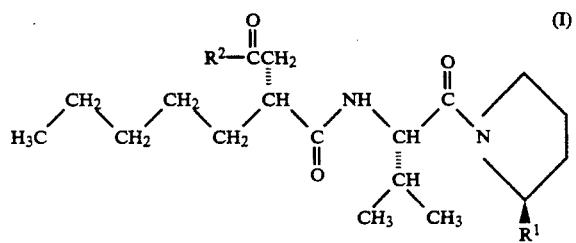

wherein $R^1$ is sulfoxymethyl or carboxyl or a substituted carboxyl group selected from carboxamide, hydroxyaminocarbonyl and alkoxycarbonyl groups; and $R^2$ is hydroxyl, alkoxy, hydroxyamino or sulfoxyamino group.

6 Claims, No Drawings

ACTINONIN DERIVATIVES AND PHARMACEUTICALLY ACCEPTABLE SALTS THEREOF

SUMMARY OF THE INVENTION

This invention relates to novel actinonin derivatives and their salts which are derived by chemical modification from a known antibiotic, actinonin, as obtainable by fermentation of a strain of actinomycetes. The novel compounds of this invention act as enzyme inhibitors and particularly have strong inhibitory activities against enkephalinase and angiotensin-converting enzymes.

BACKGROUND OF THE INVENTION

Therapeutic treatments on various diseases of mammals including man by inhibiting certain enzyme systems have hitherto been practiced widely. Thus, in therapeutically treating hypertension, cardiac failure and the like, medical treatments by administration of an enzyme inhibitor capable of inhibiting angiotensin-converting enzymes are well known. Most of such enzyme inhibitors have been derived through purely chemical synthetic routes. While, we have continued our investigations with the intention of looking for any useful enzyme inhibitor from among metabolic products of microorganisms. In the course of our investigations, we have already found that actinonin, the compound known as an antibiotic (see U.S. Pat. No. 3,240,787), inhibits a wide variety of peptidases (see "Journal of Antibiotics", 38, 1629-1630 (1985), Japanese Patent Application First Publication "Kokai" No. 15840/86 or U.S. Pat. No. 4,663,342 and JP-A "Kokai" No. 4228/86).

The previous syntheses of actinonin-related compounds have been carried out by purely synthetic means for the purpose of improving antibacterial activities of actinonin (see "Journal of the Chemical Society, Perkin Transactions 1", 1975, page 846).

We have further been proceeding with our investigations for the purpose of looking for useful enzyme inhibitors by chemical modification of actinonin with taking into consideration such fact that actinonin is obtainable by cultivating a strain of the genus Actinomycetes, *Streptomyces roseopulratus* at reasonable cost and that the molecule of actinonin has a peculiar structure consisting of L-prolinol which is obtained by the reduction of a natural amino acid, L-proline, and of a fatty acid hydroxamide. As a result, we have already found a class of actinonin derivatives which can strongly inhibit prolylendopeptidase (post-prolin-cleaving enzyme, see Japanese Patent Application First Publication "Kokai" No. 310864/88 or U.S. Pat. No. 4,929,633).

During our previous investigations on the production of novel enzyme inhibitors from which we seek for medicines useful for therapeutic treatments on such important diseases as hypertension, cardiac failure, etc., we have percieved that actinonin and derivatives thereof already known have such low levels of inhibitory activity against angiotensin-converting enzymes that are too low to be utilized in practice. Then, we have further continued our investigations on the syntheses of new actinonin derivatives with the view to providing new, useful actinonin derivatives having inhibitory activities against not only angiotensin-converting enzymes but also against enkephalinase. As a result, we have now succeeded in synthesizing a new class of actinonin derivatives having general formula (I) shown below and found them to have desired enzyme-inhibitory activities.

DETAILED DESCRIPTION OF THE INVENTION

According to this invention, there is provided a novel actinonin derivative represented by general formula (I):

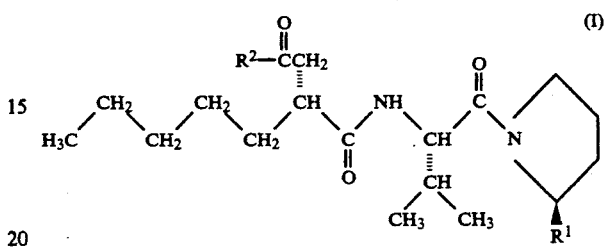

wherein $R^1$ denotes sulfoxymethyl group or carboxyl group or a substituted carboxyl group selected from carboxamido, hydroxyaminocarbonyl and alkoxycarbonyl groups, and $R^2$ denotes hydroxyl group, an alkoxy group, hydroxyamino group or sulfoxyamino group, and a salt thereof.

As typical examples of salts of actinonin derivatives of general formula (I), there may be mentioned alkali metal salts such as sodium or potassium salt or alkaline earth metal salts such as calcium or magnesium salt on such acidic groups as carboxyl and/or sulfoxyl group if present in the compounds of formula (I), or acid addition salts with pharmaceutically acceptable inorganic acids such as hydrochloric acid or sulfuric acid or with pharmaceutically acceptable organic acids such as acetic acid, succinic acid, malic acid and lactic acid on such basic groups as amino and/or imino group if present in the compounds of formula (I).

The compounds of general formula (I) according to this invention have strong inhibitory activities against angiotensin-converting enzymes and enkephalinase. The level of such inhibitory activities of the compounds of general formula (I) has been found to be about 5 to 1000 times higher than that of the starting compound, actinonin.

The new compounds of general formula (I) have also strong inhibitory activities against aminopeptidases. Further, these enzyme-inhibitory activities of the new compounds of general formula (I) are of a high enzymespecificity, and, the new compounds of this invention are characterized by their weak inhibitory activity against prolylendopeptidase, in contrast to such inhibitory activity of the actinonin derivatives we already proposed in Japanese Patnet Application "Kokai" No. 310864/88 or U.S. Pat. No. 4,929,633 above-referred to.

Typical examples of the compounds of general formula (I) according to this invention are listed below:

(1) (2R)-2-(Sulfoxyaminocarbonylmethyl)heptanoyl-L-valyl-(2S)-2-(sulfoxymethyl)pyrrolidine represented by formula (Ia)

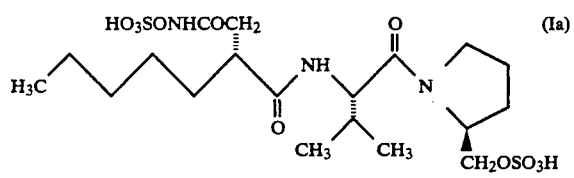

(2) (2R)-2-(Hydroxyaminocarbonylmethyl)heptanoyl-L-valyl-L-proline represented by formula (Ib)

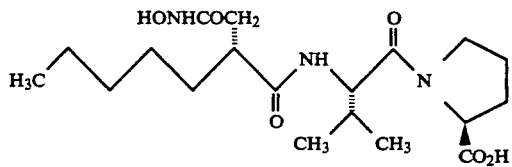

(3) (2R)-2-(Hydroxyaminocarbonylmethyl)heptanoyl-L-valyl-L-proline.methyl ester represented by formula (Ic)

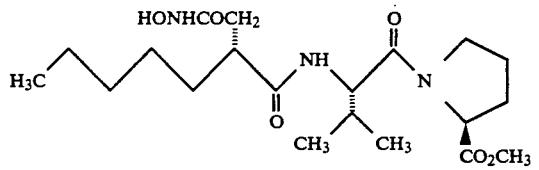

(4) (2R)-2-(Hydroxyaminocarbonylmethyl)heptanoyl-L-valyl-L-proline.hydroxamide represented by formula (Id)

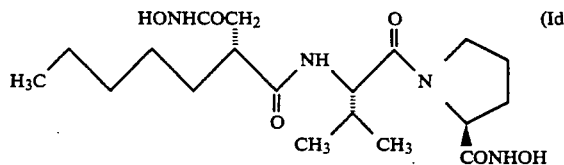

(5) (2R)-2-(Methoxycarbonylmethyl)heptanoyl-L-valyl-L-proline.hydroxamide represented by formula (Ie)

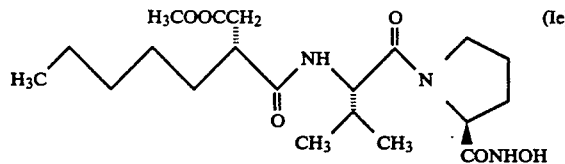

(6) (2R)-2-(Carboxymethyl)heptanoyl-L-valyl-L-proline.hydroxamide represented by formula (If)

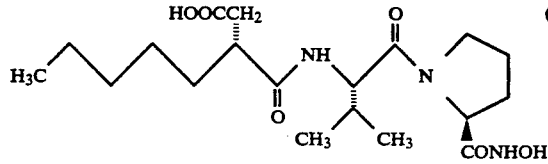

(7) (2R)-2-(Hydroxyaminocarbonylmethyl)heptanoyl-L-valyl-(2S)-2-(sulfoxymethyl)pyrrolidine represented by formula (Ig)

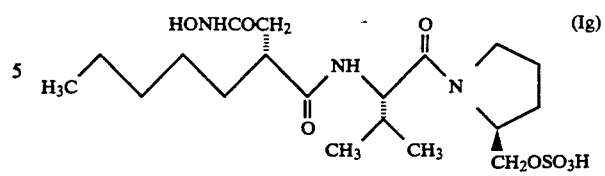

Compounds of formulae (Ia) to (Ig) listed above as typical examples of the compounds of general formula (I) according to this invention can be produced from actinonin of formula (II) shown below as starting material, typically by such processes comprising reaction steps as depicted by the following reaction schemes 1 to 5.

Reaction scheme 1

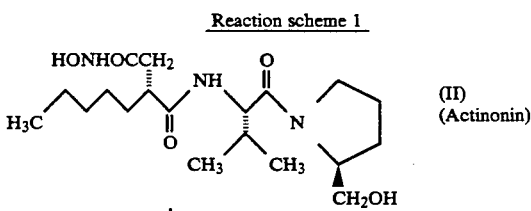

↓ (Dehydroxyamination)

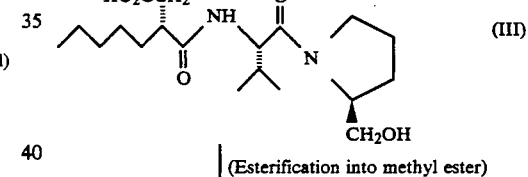

↓ (Esterification into methyl ester)

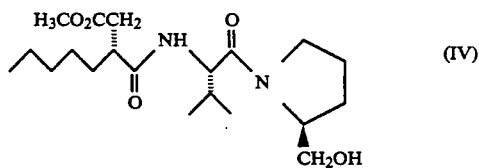

↓ (Oxidation)

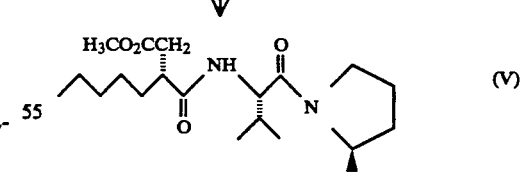

↓ (Hydroxyamination)

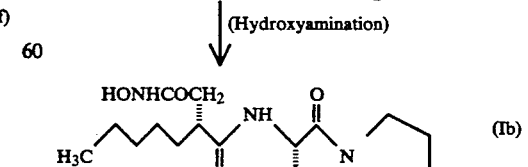

5,206,384
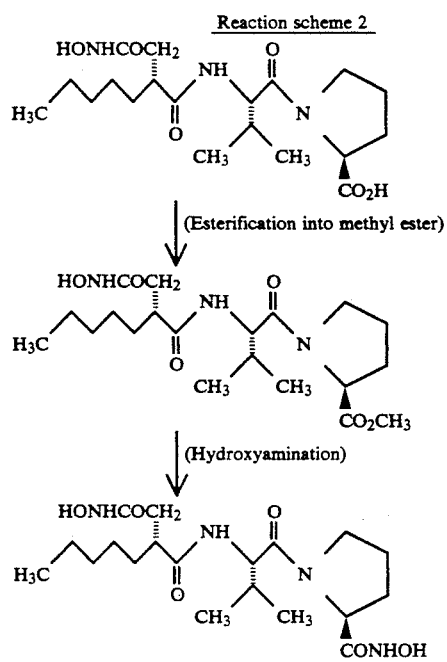
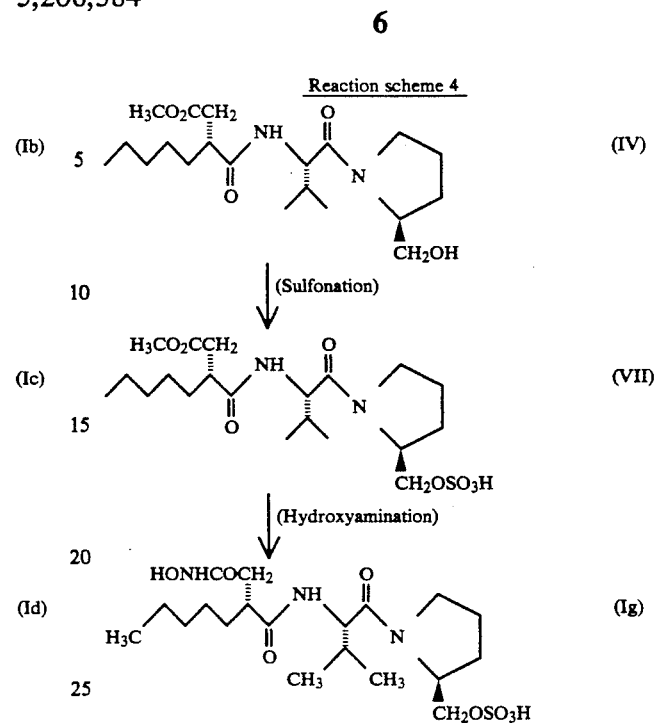
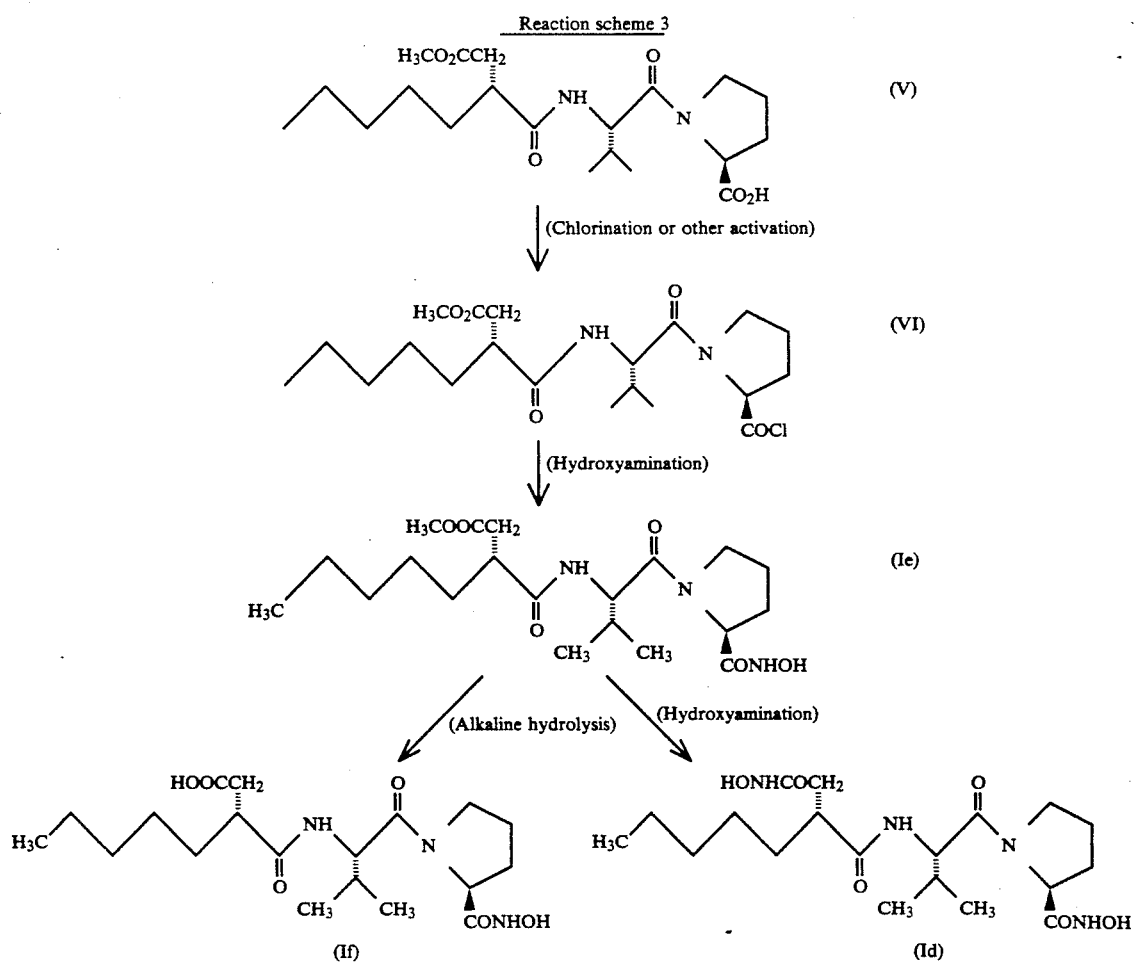

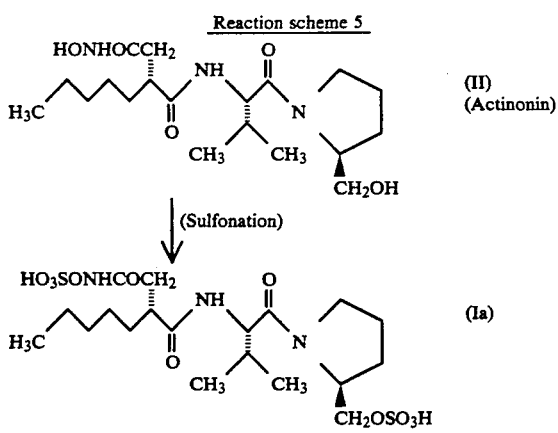

Reaction scheme 5

(II) (Actinonin)

↓ (Sulfonation)

(Ia)

The processes for the preparation of the new compounds according to this invention are now described concretely with reference to the Reaction schemes 1 to 5 of which some details of their individual reaction steps will be explained below.

Firstly, referring to Reaction scheme 1 which shows a process comprising four reaction steps to be effected or the preparation of the compound of formula (Ib), the starting compound, actinonin, of formula (II) is suspended in water and the suspension is treated with sodium periodate under ice-cooling to conduct the reaction of dehydroxyamination from actinonin, whereby the corresponding 2-carboxymethyl derivative of formula (III) is produced. The intermediate compound of formula (III) thus formed is then treated with diazomethane to conduct methylation thereof, thereby giving the corresponding methyl ester derivative of formula (IV). The intermediate compound of formula (IV) is then subjected to an oxidation so that the hydroxymethyl group existing on the pyrrolidine nucleus of said compound can be oxidized into carboxylic group. This may be conducted by any conventional oxidation treatment for the oxidation of hydroxymethyl group, preferably by treating the compound (IV) with a chromic acid-pyridine complex, whereby the corresponding proline derivative of formula (V) is formed. Finally, the compound of formula (V) is converted to the compound of formula (Ib) corresponding to such compound of general formula (I) where $R^1$ is carboxyl group and $R^2$ is hydroxyamino group, by treating the compound (V) with hydroxylamine to conduct the hydroxyamination of the methyl ester site of the compound (V).

Referring to Reaction scheme 2 which shows processes comprising reaction step(s) to be carried out for the preparation of compounds of formulae (Ic) and (Id), the compound of formula (Ib) as obtained by the process of Reaction scheme 1 is treated with diazomethane to conduct the methylation of the carboxyl group of the compound (Ib), whereby there is produced the compound of formula (Ic) corresponding to such compound of general formula (I) where $R^1$ is methoxycarbonyl group and $R^2$ is hydroxyamino group. The compound of formula (Ic) thus formed is then treated with hydroxylamine to conduct the hydroxyamination of the methoxycarbonyl group of the compound (Ib), whereby there is produced the compound of formula (Id) corresponding to such compound of general formula (I) where $R^1$ is hydroxycarbonylamino group and $R^2$ is hydroxyamino group.

Referring to Reaction scheme 3, this Reaction scheme 3 shows processes for the preparation of compounds of formulae (Ie), (Id) and (If), wherein compound of general formula (I) where $R^2$ is hydroxyl group or methoxy group according to this invention, namely the compound of formula (If) or (Ie) may be derived from compound of formula (IV) or (V) as obtained by the process of Reaction scheme 1. Compound of general formula (I) where $R^1$ is hydroxyaminocarbonyl group, such as compounds of formula (Ie), (Id) or (If) may be derived by modification of the proline moiety of the compound of formula (V).

To be concrete, compound (V) is chlorinated with a chlorinating agent to give the corresponding acid chloride compound (VI). As the chlorinating agent, oxalyl chloride, thionyl chloride, phosphorus pentachloride, etc. can be used, among which thionyl chloride is preferred and convenient to give the compound (VI) in a high yield. The compound (VI) is then treated with hydroxylamine to effect the hydroxyamination and thereby from the compound of formula (Ie) which is corresponding to such compound of general formula (I) where $R^1$ is hydroxyaminocarbonyl group and $R^2$ is methoxy group. The compound (Ie) is then hydrolyzed with an alkali metal hydroxide or carbonate in an aqueous solution under alkaline condition for the removal of the methoxy group from the compound (Ie) to give the compound of formula (If) which is corresponding to such compound of general formula (I) where $R^1$ is hydroxyaminocarbonyl group and $R^2$ is hydroxyl group. In the same Reaction scheme 3, compound (Ie) may be reacted with hydroxylamine to give compound (Id).

Referring to Reaction scheme 4 which shows a process comprising reaction steps to be effected for the preparation of the compound of formula (Ig), compound of formula (IV) as obtained in the process of Reaction scheme 1 is used as starting compound. Thus, the compound(IV) is sulfonated by treating with pyridine-sulfur trioxide complex so that the corresponding sulfoxymethyl compound of general formula (VII) is produced. This compound (VII) is then hydroxyaminated by reaction with hydroxylamine to give the compound of formula (Ig) which is corresponding to such compound of general formula (I) where $R^1$ is sulfoxymethyl group and $R^2$ is hydroxyamino group.

Finally, referring to Reaction scheme 5 which shows a process comprising a reaction step to be taken for the preparation of the compound of formula (Ia), actinonin of formula (II) is suspended in pyridine and the suspension is treated with a pyridine-sulfuric acid anhydride complex, namely pyridine-sulfur trioxide complex under ice-cooling to conduct O-sulfonation reaction, giving the corresponding bis-O-sulfo derivative as the desired product, i.e. the compound of formula (Ia) which is corresponding to such compound of general formula (I) where $R^1$ is sulfoxymethyl and $R^2$ is sulfoxyamine group. As the O-sulfonating reagent, any combination of sulfuric acid anhydride ($SO_3$) with an organic or inorganic base may be used, but the use of a pyridine-sulfuric acid anhydride complex dissolved in pyridine as the reaction medium is preferred and convenient to form the compound of formula (Ia) in a high yield.

Now, the physiological properties, particularly the inhibitory activities against some enzymes, of typical compounds of general formula (I) according to this invention will be demonstrated.

(A) The compounds of general formula (I) according to this invention possess enzyme-inhibitory activities as above-mentioned and are expectable to be useful in the therapeutic treatments of certain diseases of mammalian. Thus, we have tested the enzyme-inhibitory activities of some typical compounds of this invention against angiotensin-conversion enzyme (ACE) which participates in the control of blood-pressure in mammalian animals by converting angiotensin I, a peptide-type hormone in brain, into angiotensin II. The determination of ACE-inhibitory activity was carried out in accordance with the method described in "Analytical Biochemistry", 84, 361 (1978) and the activity was estimated in term of the concentration (mole concentration, M) of each compound tested at which the activity of the enzyme can be inhibited by 50% ($IC_{50}$). The test results are shown in Table 1.

TABLE 1

| ACE-inhibitory activity of compounds of this invention | |
|---|---|
| Test compound | $IC_{50}$ (M) |
| Compound of formula (Ia) | $9.2 \times 10^{-5}$ |
| Compound of formula (Ib) | $2.8 \times 10^{-5}$ |
| Compound of formula (Id) | $5.3 \times 10^{-7}$ |
| Compound of formula (Ig) | $4.3 \times 10^{-4}$ |
| Actinonin (as Referential compound) | $5.9 \times 10^{-4}$ |

As is clear from the test results of Table 1, compounds of formulae (Ia), (Ib) and (Id) of this invention each exhibited an ACE-inhibitory activity about 10 to 1000 times stronger than that of actinonin as reference. Accordingly, the compounds of general formula (I) according to this invention possess remarkably enhanced ACE-inhibitory activities as compared with that of actinonin.

It is already known in the art that compounds having an ACE-inhibitory activity generally exhibit an antihypertension, i.e. blood-pressure reducing activity (refer to, for example, "Japan Clinics", a special number for the spring of 1986, No. 540 for the consecutive number of volumes, pages 481–488, issued on Mar. 3, 1986; "Medicinal Research Reviews", Vol 5, No. 4, 483–531 (1985), M. J. Wyvratt and A. A. Patckett "Recent Developments in the Design of Angiotension-Converting Enzyme Inhibitors"; and "An Outline of Clinical Medical Treatments" vol. 11, "Diseases in Circulatory System", pages 241–243 published by Information Development Research Institute). Since the compounds of this invention exhibit a high ACE-inhibitory activity as demonstrated above, it is apparent that they will be effective as antihypertensive agent.

(B) The compounds of general formula (I) according to this invention further possess enkephalinase-inhibitory activity. Enkephalinase is a peptide type hormone in brain and acts as an enzyme which decomposes enkephaline and thus exhibits an analgesic activity. It is expectable that an enkephalinase-inhibitor is effective as a non-addictive analgesic agent.

$IC_{50}$ concentrations (M concentration) of some typical compounds of this invention which can inhibit enzymatic activity of enkephalinase by 50% were measured. The test results are shown in Table 2.

TABLE 2

| Enkephalinase-inhibitory activity of compounds of this invention | |
|---|---|
| Test compound | $IC_{50}$ (M) |
| Compound of formula (Ia) | $1.4 \times 10^{-5}$ |
| Compound of formula (Ib) | $3.1 \times 10^{-7}$ |
| Compound of formula (Id) | $1.2 \times 10^{-6}$ |

TABLE 2-continued

| Enkephalinase-inhibitory activity of compounds of this invention | |
|---|---|
| Test compound | $IC_{50}$ (M) |
| Compound of formula (Ig) | $4.1 \times 10^{-6}$ |
| Actinonin (as reference) | $5.6 \times 10^{-6}$ |

As is apparent from the test results of Table 2, the compound of formula (Ib) exhibited an enkephalinase-inhibitory activity more than 10 times stronger than that of actinonin as reference.

Now, this invention is illustrated with reference to the following Examples which demonstrate the preparation of the compounds of general formula (I).

EXAMPLE 1

Preparation of the compound of formula (Ib)

(a) Synthesis of compound of formula (III)

Actinonin (1 g) was suspended in a mixture of water (100 ml) and ethyl ether (20 ml) and 1.5N aqueous sodium periodate solution (25 ml) was added to the resulting suspension under stirring. Stirring was continued for 2 hours at room temperature to conduct the reaction. The resulting reaction solution was saturated with sodium chloride and then extracted with ethyl ether (50 ml×3). The ether layers as the extracts were combined and then extracted with an aqueous saturated sodium hydrogen carbonate solution (20 ml×3). The aqueous layers as the extracts were combined and then acidified to pH<2 with 2N HCl. The acidified aqueous solution was saturated with sodium chloride and then extracted with ethyl ether (50 ml×3). The resulting extracts in ether were combined, dried over anhydrous sodium sulfate and then concentrated under a reduced pressure to afford the compound of formula (III) as the dehydroxyaminated intermediate given in Reaction scheme 1 (795 mg; yield 83%).

Melting point: 40°–42° C.

FD-MS (m/z): 371 (M+H)

IR max (cm$^{-1}$): 2800 (—OH), 1720 (—CO),

NMR(400 MHz, CDCl$_3$): 0.86(3H, t, J=6.7 Hz, —CH$_3$), 0.94 and 0.96(each 3H, d, J=6.6 Hz, Me of Val), 1.24(6H, broad, —CH$_2$×3), 1.44(2H, m, —CH$_2$), 1.5–1.8(2H, m), 1.8–2.1(4H, m), 2.46(1H, m, —CH—N<) 4.24(1H, m), 4.60(1H, t, J=8.5, —CO-CH—<), 7.39(1H, d, J=9.2, —NH)

(b) Synthesis of compound of formula (IV)

The compound of formula (III) (695 mg) obtained in step (a) above was dissolved in ethyl ether (14 ml) and a solution of diazomethane in ethyl ether was added to the resulting solution at room temperature to cause the methylation. After confirming the completed methylation reaction, the ether layer of the reaction solution was washed with water (5 ml×4), dried over anhydrous sodium sulfate and then concentrated under a reduced pressure to yield the compound of formula (IV), the methyl ester derivative (710 mg; yield 98%).

[α]$_D$ —49.0° (c 1.0, methanol),

FD-MS (m/z): 385 (M+1),

IR(KBr): 1730(—CO$_2$), 1190, 1160 cm$^{-1}$

NMR(400 MHz, CDCl$_3$) (TMS): 0.86(3H, t, J=6.8 Hz, —CH$_3$), 1.25(6H, broad, —CH$_2$×3), 1.4(1H, m, —CH—), 1.60(2H, m, —CH—), 1.8–2.2(4H, m, —CH— and —CH$_3$) 2.42(1H, q, J=3.9 and 16.0, —CHCO), 3.49(1H, dt, J=2.9 and 7.3—CHN<), 3.55–3.7(5H, s and m, CH$_3$O$_2$C— and CH$_2$OH), 3.90(1H, m, J=2.9 and 7.3—CHN<), 4.23(1H, dd, J=3.1 and 7.1, —CH$_2$—), 4.62(1H, dd, J=7.1 and 9.0, —COCN<), 6.44(1H, d, J=9.0, NH)

(c) Synthesis of the compound of formula (V)

The compound of formula (IV) (637 mg) obtained in step (b) above was dissolved in dry dimethylformamide (16 ml) and pyridinium chlorodichromate (PDC) (1.43 g) was added to the resulting solution. The mixture was stirred at room temperature overnight to conduct the oxidation reaction intended, whereupon a further amount (0.72 g) of PDC was added to the reaction mixture and the stirring was continued at room temperature for further 5 hours to complete the reaction. After adding water (48 ml), the resulting reaction solution was extracted with ethyl ether (48 ml×4). The ether layers obtained as the extracts were combined together, washed with water (10 ml×2) and extracted with an aqueous saturated sodium hydrogen carbonate solution (20 ml×3). The aqueous extracts obtained were combined, adjusted to pH 2-3 with addition of a 10% aqueous potassium hydrogen sulfate solution and then extracted with ethyl ether (48 ml×3). The ether layers as the extracts were combined, dried over anhydrous sodium sulfate and then concentrated under a reduced pressure to give the compound of formula (V), the carboxylic acid derivative (377 mg; yield 57%).

Melting point: 102°-104° C.,
$[\alpha]_D$ −76° (c 1.0, methanol),
FD-MS: 399 (M+H),
IR(KBr): 2700-2200(—COOH), 1730(ester), 1610(—CO$_2$)cm$^{-1}$
NMR(400 MHz, CDCl$_3$): 0.86(3H, t, J=6.8, —CH$_3$), 0.97 and 1.03(each 3H, d, —CH$_3$, of Val), 1.1-1.4(6H, m, —CH$_2$—×3), 1.4-1.6(2H, m, —CH$_2$—), 1.9-2.3(5H, m, —CH<, —CH$_2$×2 of Pro), 2.32(1H, dd, J=6.1 and 14.7, —CHNHOH), 2.80(1H, m, —COCH<), 3.75 and 3.89(2H, m —CH$_2$— of Pro), 4.25(1H, dd, J=5.4 and 8.5, —CH— of Pro), 4.47(1H, d, J=8.9, —COCH<), Elementary analysis (for C$_{20}$H$_{34}$H$_2$O$_6$.1/4H$_2$O) Calcualted: C 59.66, H 8.80, N 6.96% Detected: C 59.66, H 8.80, N 6.91%

(d) Synthesis of the compound of formula (Ib)

Potassium hydroxide (277 mg) was dissolved in methanol (0.7 ml) and the resulting solution was added with a methanolic solution (1 ml) of hydroxylamine hydrochloride (143 mg) at 0° C. The precipitate thus formed was filtered off and the filtrate was added to a methanolic solution (0.1 ml) of the compound of formula (V) (39.9 mg) obtained in step (c) above and the mixture was stirred overnight to conduct the reaction intended. To the resulting reaction solution was added an amount of Dowex 50W×2 (H+) resin, a strongly acidic cation exchange resin commercially available from Dow Chemical Co., which had been washed with methanol, so that the pH of the reaction solution was adjusted to 2. The resin was filtered off and the filtrate was concentrated under a reduced pressure to leave a residue, to which was then added an aqueous solution (1 ml) of sodium hydrogen carbonate (21.8 mg) to dissolve the residue. The resultant solution was subjected to adsorption in a column of an adsorbent resin, "Diaion" HP-20 (4 ml) (a column of 10 mm diameter and 50 mm height), and the resin column was then developed successively with water and 5% aqueous methanol to elute the desired product. Thus, there was obtained the compound of formula (I), the hydroxamic acid derivative, given in Reaction scheme 1 (28 mg; yield 68%).

Melting point: 153°-154° C.,
$[\alpha]_D$ −83.1° (c 1.0, methanol)
IR(KBr): 3250, 1620, 1450, 1390 cm$^{-1}$
NMR(400 MHz, CDCl$_3$): 0.86(3H, t, J=6.8 Hz, —CH$_3$), 0.97 and 1.03(each 3H, d, J=6.7, —CH$_3$ of Val), 1.1-1.4(6H, m, —CH$_2$—×3), 1.4-1.6(2H, m, —CH$_2$—), 1.9-2.3(5H, m, —CH< and —CH$_2$ of Pro), 2.32(1H, dd, J=6.1 and 14.7, —CHNHOH), 4.25(1H, dd, J=5.4 and 8.5, —C2H— of Pro), 4.47(1H, d, J=8.9, COCH<), 7.07(1H, d, J=8.2, —CONH)

EXAMPLE 2

Preparation of the compound of formula (Ic)

The compound of formula (Ib) (102 mg) obtained in Example 1 was dissolved in water (3.1 ml) and the pH of the resulting solution was adjusted to 2 with addition of a 10% aqueous potassium hydrogen sulfate solution. The acidic solution so obtained was concentrated and then extracted with methanol (14.4 ml×2). The precipitate was filtered off and the filtrate was concentrated to leave a residue, which was then dissolved in methanol (14.4 ml). A solution of diazomethane in ethyl ether was slowly added to the resulting methanolic solution to effect the formation of the methyl ester intended. After confirming the completion of the methyl ester-forming reaction, the resulting reaction solution was concentrated under a reduced pressure. The residue was dissolved in ethyl ether (28.8 ml) and the ethereal solution was washed with water (7.2 ml×2), dried over anhydrous sodium sulfate and then concentrated under a reduced pressure to afford the compound of formula (Ic), the methyl ester derivative, (86 mg; yield 84%).

Melting point: 174°-175° C.
$[\alpha]_D$ −95.1° (c 1.0, methanol),
FD-MS: 414 (M+H)
IR(KBr): 1745(—COO−), 1195, 1170 cm$^{-1}$
NMR(400 MHz, CDCl$_3$): 0.88(3H, t, J=6.7, —CH$_3$), 1.00 and 1.02(each 3H, d, J=6.7, —CH$_3$ of Val), 1.26(6H. ,. —CH$_2$ 2—×3), 1.40 and 1.54(each 1H, m —CH$_2$), 1.9-2.1(3H, m, C4H$_2$ and C3H of Pro), 2.1-2.4(3H, m, C3H of Pro and —CH$_2$CO), 2.78(1H, m, COCH<), 4.39(2H, m, C2H of Pro and COCH<)

EXAMPLE 3

Preparation of the compound of formula (Ie)

The compound of formula (V) (107.6 mg) obtained in Example 1(c) was dissolved in methylene chloride (2.7 ml). To the solution, there were added successively at 0° C. triethylamine (49 μl) and ethyl chloroformate (31 μl), and the resulting mixture was stirred at that temperature for 30 minutes to conduct the reaction. To the reaction solution containing the acid chloride derivative of formula (VI) produced, was added a solution of hydroxylamine hydrochloride (56.2 mg) in methanol (2.7 ml) which had contained TEA (112.6 μl) added at 0° C. The resulting reaction mixture was stirred for 2 hours to effect the reaction. Methylene chloride (5.4 ml) was added to the resulting reaction solution and the mixture was washed with an aqueous saturated sodium chloride solution which had been adjusted to pH 2 with the addition of 1N HCl (2 ml×3), and then said mixture was dried over anhydrous sodium sulfate and then concentrated under a reduced pressure to yield a crude product (120 mg). This was dissolved in water (6.4 ml) containing sodium hydrogen carbonate (24.4 mg; 1.1 eq.) and the solution was passed through a column of "Diaion" HP-20 resin (11 ml; a column of 10 mm diameter and 135 mm height) for adsorption of the desired compound, and the resin column was then developed with 20 ml each of water, 5% methanol, 20% methanol, 50% methanol and 80% methanol, successively. The fractions of the eluate containing the desired compound were combined and concentrated to dryness to yield the compound of formula (Ie), the hydroxamic acid derivative, (85.6 mg; yield 73%).

Melting point: 49°–50° C.,
$[\alpha]_D$ −80.9° (c 1.0, methanol),
FD-MS: 413(M+)
IR(KBr): 3250, 1750, 1620, 1530, 1420 cm$^{-1}$
NMR(400 MHz, CD$_3$OD): 0.88(3H, t, J=6.9, —CH$_3$), 0.99 and 1.00(each 3H, d, J=6.8, —CH$_3$×2 of Val), 1.25(6H, broad M, —CH$_2$—×3), 1.40 and 1.52(each 1H, m, —CH$_2$—), 1.9–2.2(5H, m, —CH<, C3H$_2$ and C4H$_2$ of Pro), 2.41(1H, dd, J=4.9 and 16.4, —CHCO), 2.61(1H, dd, J=9.9 and 16.4, —CHCO), 2.77(1H, m, —COCH<), 3.63(3H, s, CH$_3$CO), 3.68 and 3.95(each 1H, m, C5H of Pro), 4.25(1H, dd, J=5.6 and 7.4, C2H of Pro), 4.40(1H, d, J=8.7, —CHCH<)

EXAMPLE 4

Preparation of the compound of formula (Id)

Potassium hydroxide (847 ml) was dissolved in methanol (2.1 ml) and the resulting solution was added with a methanolic solution (3.1 ml) of hydroxylamine hydrochloride (438 mg) at 0° C. The precipitate formed was filtered off and the filtrate was added to a methanolic solution (3.3 ml) of the compound of formula (Ie) obtained in Example 3, and the mixture so obtained was stirred at room temperature for 3 hours to conduct the hydroxyamination reaction. To the resulting reaction solution was added an amount of Dowex 50W×2(H+) resin which had been washed with methanol, so that the pH of the solution was adjusted to 2. The resin was removed by filtration and the filtrate was concentrated under a reduced pressure to leave a residue. An aqueous solution (20 ml) of sodium hydrogen carbonate (113 mg) was added to the residue to dissolve the latter. The resulting solution was charged into a column of "Diaion" HP-20 resin (10 ml; a column of diameter 10 mm and 120 mm height) for adsorption of the desired compound and the resin column was then developed with water, 5% methanol, 20% methanol and 50% methanol, successively. The fractions of the eluate containing the desired compound were combined and concentrated to dryness to obtain the compound of formula (Id), the dihydroxamic acid derivative (81 mg; yield 58%).

Melting point: 169°–171° C.,
FD-MS: 415
IR(KBr): 1670, 1610, 1440, 1060 cm$^{-1}$
NMR(400 MHz, D$_2$O): 0.83(3H, d, J=6.7 Hz, —CH$_3$), 0.94 and 0.96(each 3H, d, J=6.7, —CH$_3$ of Val), 1.27(6H, m, —CH$_2$×2), 1.48(2H, m, —CH$_2$), 1.8–2.5(7H, m, —CH<, —CH$_2$—×2 of Pro, —CH$_2$—CONHOH), 2.79(1H, m, —COCH<), 3.72 and 3.94(each 1H, m, —C$_5$H$_2$ of Pro), 4.25(1H, m, C$_2$H of Pro), 4.42(1H, m, —COCH<)

The compound of formula (Ia), namely (2R)-2-(sulfoxyaminocarbonylmethyl)heptanoyl-L-valyl-(2S)-2-(sulfoxymethyl)pyrrolidine was synthetized by sulfonation of actionin with pyridine-sulfur trioxide complex and exhibited the following properties:

Melting point: 108°–115° C.
IR(KBr): 1650(CONH),1250–1270(—SO$_3$—), 1160(—SO$_3$—), cm$^{-1}$
NMR(CDCl$_3$), δ ppm: 0.74(3H, d), 0.78(3H, t), 0.85(3H, d), 1.13(6H, m), 1.80 and 1.52(2H, m), 1.80–2.02(4H, m), 2.15(1H, m), 2.44(1H, dd), 2.58(1H, m), 2.78(1H, dd) 3.57(1H, m), 3.64(3H, m), 3.72(1H, m), 4.42(1H, dd), 4.49(1H, dd), 6.18(1H, d)

The compound of formula (If), namely (2R)-2-(carboxymethyl)heptanoyl-L-valyl-L-proline hydroxamide was synthetized by alkaline hydrolysis of the compound of formula (Ie) and exhibited the following properties:

Melting point: 134°–139° C.
IR(KBr): 2800 (—OH), 1735 (CO), cm$^{-1}$
NMR(CDCl$_3$), δ ppm: 0.74(3H, d, —CH$_3$), 0.76(3H, t, —CH$_3$), 0.83(3H, d, J=6.9 Hz. —CH$_3$), 1.13(6H, m, —CH$_2$—×2), 1.30 and 1.51(each 1H, m, —CH$_2$—), 1.8–2.05(4H, m. Pro), 2.13(1H, m, Pro), 2.44(1H, dd, J=4.9 and 16.7, —CH$_2$CO), 2.55(1H, m, —CHCO), 2.77(1H, dd, J=8.8 and 16.7, —CHCO), 3.57(1H, m, Pro), 3.64(3H, J=5.3 and 8.6, Pro), 3.72(1H, m, Pro), 4.40(1H, dd, J=5.3 and 8.6, Pro), 4.49(1H, dd, J=6.7 and 9.0, —CHCO), 6.19(1H, d, J=9.0, NH)

The compound of formula (Ig), namely (2R)-2-(hydroxyaminocarbonylmethyl)heptanoyl-L-valyl-(2S)-2-(sulfoxymethyl)pyrrolidine was prepared and exhibited the following properties:

Melting point: 122°–127° C.
IR(KBr): 1750(CO), 1659(CONH), 1260–1280(—SO$_3$—), 1116(—SO$_3$—), cm$^{-1}$
NMR(CDCl$_3$), δ ppm: 0.74(3H, d), 0.76(3H, t), 0.85(3H, d), 1.12(6H, m), 1.28 and 1.50(2H, m), 1.78–2.02(4H, m), 2.15(1H, m), 2.44(1H, dd), 2.58(1H, m), 2.78(1H, dd), 3.57(1H, m), 3.64(3H, m), 3.75(1H, m), 4.43(1H, dd), 4.49(1H, dd), 6.20(1H, d)

What is claimed is:

1. An actinonin derivative represented by general formula (I):

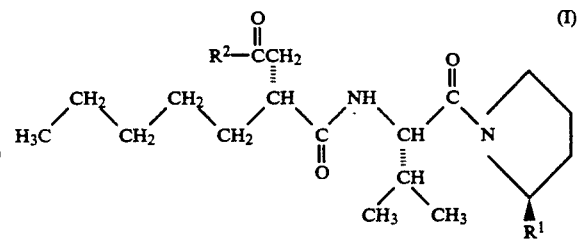

wherein R$_1$ denotes sulfoxymethyl group or a substituted carboxyl group selected from carboxamide and hydroxyaminocarbonyl groups, and R$^2$ denotes hydroxyl group, an alkoxy group, hydroxyamino group or sulfoxyamino group, and a pharmaceutically-acceptable salt thereof.

2. An actinonin derivative according to claim 1 and having general formula (I) where R$^1$ is sulfoxymethyl group —CH$_2$OSO$_3$H and R$^2$ is sulfoxyamino group —NHOSO$_3$H, namely said actinonin derivative being (2R)-2-(sulfoxyaminocarbonylmethyl)heptanoyl-L-valyl-(2S)-2-(sulfoxymethyl)pyrrolidine, and a pharmaceutically acceptable salt thereof.

3. An actinonin derivative according to claim 1 and having general formula (I) where R$^1$ is hydroxyaminocarbonyl group —CONHOH and R$^2$ is hydroxyamino group —NHOH, namely said actinonin derivative being (2R)-2-(hydroxyaminocarbonylmethyl)heptanoyl-L-valyl-L-proline.hydroxamide, and a salt thereof.

4. An actinonin derivative according to claim 1 and having general formula (I) where R$^1$ is hydroxyaminocarbonyl group —CONHOH and R$^2$ is methoxy group —OCH$_3$, namely said actinonin derivative being (2R)-2-(methoxycarbonylmethyl) heptanoyl-L-valyl-L-proline.hydroxamide, and a salt thereof.

5. An actinonin derivative according to claim 1 and having general formula (I) where $R^1$ is hydroxyaminocarbonyl group —CONHOH and $R^2$ is hydroxyl group —OH, namely said actinonin derivative being (2R)-2-(carboxymethyl)heptanoyl-L-valyl-L-proline.-hydroxamide, and a salt thereof.

6. An actinonin derivative according to claim 1 and having general formula (I) where $R^1$ is sulfoxymethyl group —$CH_2OSO_3H$ and $R^2$ is hydroxyamino group —NHOH, namely said actinonin derivative being (2R)-2-(hydroxyaminocarbonylmethyl)heptanoyl-L-valyl-(2S)-2-(sulfoxymethyl) pyrrolidine, and a salt thereof.

* * * * *